United States Patent
Gan

(10) Patent No.: US 11,919,920 B2
(45) Date of Patent: Mar. 5, 2024

(54) TERPENE GLYCOSIDE DERIVATIVES AND USES THEREOF

(71) Applicant: Firmenich SA, Satigny (CH)

(72) Inventor: Xian-Wen Gan, Shanghai (CN)

(73) Assignee: Firmenich SA, Satigny (CH)

( * ) Notice: Subject to any disclaimer, the term of this patent is extended or adjusted under 35 U.S.C. 154(b) by 485 days.

(21) Appl. No.: 17/252,266

(22) PCT Filed: Sep. 25, 2019

(86) PCT No.: PCT/EP2019/075782
§ 371 (c)(1),
(2) Date: Dec. 14, 2020

(87) PCT Pub. No.: WO2020/064787
PCT Pub. Date: Apr. 2, 2020

(65) Prior Publication Data
US 2021/0269469 A1 Sep. 2, 2021

(30) Foreign Application Priority Data
Sep. 29, 2018 (WO) ................ PCT/CN2018/108629

(51) Int. Cl.
| | |
|---|---|
| *C07H 13/08* | (2006.01) |
| *A23L 2/60* | (2006.01) |
| *A23L 27/30* | (2016.01) |
| *C12P 19/14* | (2006.01) |
| *C12P 19/56* | (2006.01) |

(52) U.S. Cl.
CPC ................ *C07H 13/08* (2013.01); *A23L 2/60* (2013.01); *A23L 27/36* (2016.08); *C12P 19/14* (2013.01); *C12P 19/56* (2013.01); *A23V 2002/00* (2013.01)

(58) Field of Classification Search
CPC .................................. C12P 19/56; C07H 13/08
See application file for complete search history.

(56) References Cited

PUBLICATIONS

Ryoji et al., Sweet Diterprene Glycosides of Leaves of Stevia: Rebaudiosides A, D, and E and their relating glycoside as well as Relationship between their Sweetness and Chemical Structure,, Journal of the Chemical Society of Japan, No. 5, (1981), pp. 726-735 (Year: 1981).*

Adari et al., "Synthesis of rebaudioside-A by enzymatic transglycosylation of stevioside present in the leaves of Stevia rebaudiana Bertoni", Food Chemistry, 200, (2016), pp. 154-158. (Year: 2016).*

\* cited by examiner

*Primary Examiner* — Elizabeth Gwartney
(74) *Attorney, Agent, or Firm* — Robert S. Dailey

(57) ABSTRACT

The present disclosure relates generally to terpene glycosides, such as certain such compounds extracted from *Stevia rebaudiana bertoni*, *Rubus suavissimus*, or *Siraitia grosvenorii*. The disclosure also provides for the use of such compounds as food ingredients, flavors, and sweeteners, and related methods. The disclosure also provides ingestible compositions comprising such compounds, as well as processes for extracting such compounds selectively from certain plant sources.

4 Claims, 3 Drawing Sheets

TERPENE GLYCOSIDE DERIVATIVES AND USES THEREOF

CROSS-REFERENCE TO RELATED APPLICATIONS

The present application is the United States national stage patent application of PCT Application No. PCT/EP2019/075782, filed Sep. 25, 2019, which claims the benefit of priority of PCT Application No. PCT/CN2018/108629, filed Sep. 29, 2018, which is hereby incorporated by reference as though set forth herein in its entirety.

TECHNICAL FIELD

The present disclosure relates generally to terpene glycosides, such as certain such compounds extracted from *Stevia rebaudiana bertoni*, *Rubus suavissimus*, or *Siraitia grosvenorii*. The disclosure also provides for the use of such compounds as food ingredients, flavors, and sweeteners, and related methods. The disclosure also provides ingestible compositions comprising such compounds, as well as processes for extracting such compounds selectively from certain plant sources.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami.

Sweetness is the taste most commonly perceived when eating foods rich in sugars. Mammals generally perceive sweetness to be a pleasurable sensation, except in excess. Caloric sweeteners, such as sucrose and fructose, are the prototypical examples of sweet substances. Although a variety of no-calorie and low-calorie substitutes exist, these caloric sweeteners are still the predominant means by which comestible products induce the perception of sweetness upon consumption.

Metabolic disorders and related conditions, such as obesity, diabetes, and cardiovascular disease, are major public health concerns throughout the world. And their prevalence is increasing at alarming rates in almost every developed country. Caloric sweeteners are a key contributor to this trend, as they are included in various packaged food and beverage products to make them more palatable to consumers. In many cases, no-calorie or low-calorie substitutes can be used in foods and beverages in place of sucrose or fructose. Even so, these compounds impart sweetness differently from caloric sweeteners, and a number of consumers fail to view them as suitable alternatives. Moreover, such compounds may be difficult to incorporate into certain products. In some instances, they may be used as partial replacements for caloric sweeteners, but their mere presence can cause many consumers to perceive an unpleasant astringency. Therefore, lower-calorie sweeteners still face certain challenges to their adoption.

Terpene glycosides, such as steviol glycosides from *Stevia* (*Stevia rebaudiana bertoni*) extracts, rubusoside from blackberry leaf (*Rubus suavissimus*) extracts, and mogrosides from monk fruit (*Siraitis grosvenorii*) extracts, are natural low-calorie sweeteners. But these products, like many other low-calorie sugar alternatives, have negative taste attributes, such as bitterness, lingering aftertaste, or licorice flavor. Transglucosylation provides a way of mitigating some of these negative taste attributes. But many of the presently disclosed glucosylated low-calorie sweeteners continue to exhibit negative taste attributes that prevent their widespread adoption. Thus, there is a continuing need to develop glucosylated products and transglucosylation methods that can provide more effective mitigation of negative taste attributes.

SUMMARY

In a first aspect, the disclosure provides methods of making a glucosylated terpene glycoside, the method comprising: (a) providing an aqueous composition comprising a β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,4 glucosidic bond between the terpene glycoside moiety and one of the one or more β-glucosyl sugar moieties. In some embodiments, the reacting comprises incubating the aqueous composition. In some embodiments, the aqueous composition is an aqueous solution. In some embodiments, the β-glucosyl sugar compound is cellobiose.

In a second aspect, the disclosure provides methods of reducing an unpleasant taste of a terpene glycoside, the method comprising: (a) providing an aqueous composition comprising an β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,4 glucosidic bond between the terpene glycoside moiety and one of the one or more β-glucosyl sugar moieties. In some embodiments, the reacting comprises incubating the aqueous composition. In some embodiments, the aqueous composition is an aqueous solution. In some embodiments, the β-glucosyl sugar compound is cellobiose.

In some embodiments of the first or second aspects, the terpene glycoside is stevioside, rebaudioside A, rebaudioside B, rebaudioside C, rebaudioside D, rebaudioside E, rebaudioside F, rebaudioside G, rebaudioside M, dulcoside A, steviolbioside, rubusoside, terpene glycosides found in *Stevia rebaudiana bertoni* plants, terpene glycosides found in *Rubus suavissimus* plants, terpene glycosides found in *Siraitis grosvenorii* plants, or any mixtures thereof.

In some embodiments of the first or second aspects, the beta-glucosyl sugar compound is cellobiose.

In some embodiments of the first or second aspects, the glucosylated terpene glycoside is mono β-1,4 glucosylated stevioside, mono β-1,4 glucosylated rebaudioside A, mono β-1,4 glucosylated rebaudioside B, mono β-1,4 glucosylated rebaudioside C, mono β-1,4 glucosylated rebaudioside D, mono β-1,4 glucosylated rebaudioside E, mono β-1,4 glucosylated rebaudioside F mono β-1,4 glucosylated rebaudioside G, mono β-1,4 glucosylated rebaudioside M, mono β-1,4 glucosylated dulcoside A, mono β-1,4 glucosylated steviolbioside, mono β-1,4 glucosylated rubusoside, or any mixtures thereof.

In a third aspect, the disclosure provides a compound of formula I:
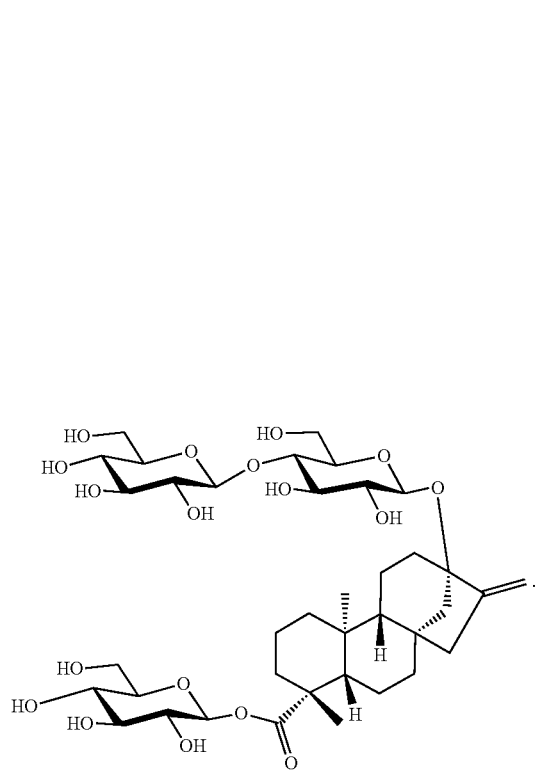
I
In a fourth aspect, the disclosure provides a compound of formula II:
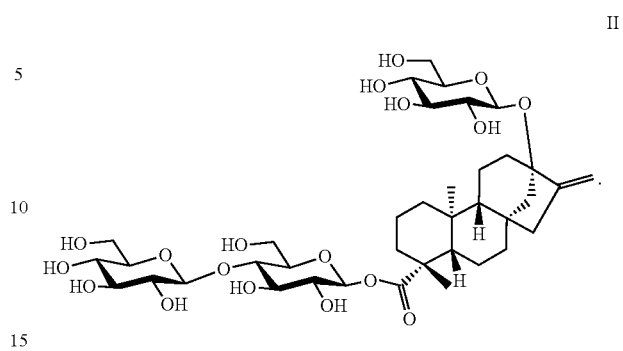
II
In a fifth aspect, the disclosure provides a compound of formula III:
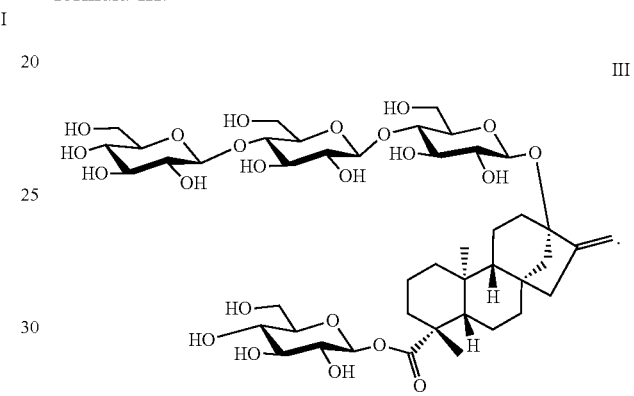
III
In a sixth aspect, the disclosure provides a compound of formula IV:
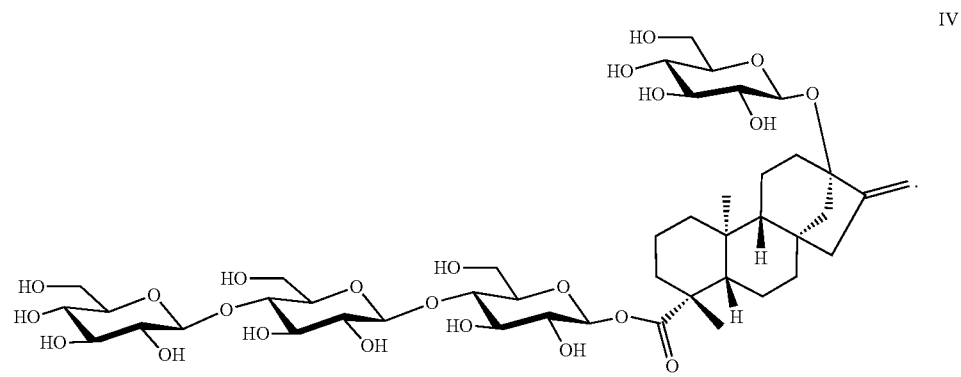
IV In a seventh aspect, the disclosure provides a composition comprising at least one glucosylated terpene glycoside selected from the group consisting of: mono β-1,4 glucosylated stevioside, mono β-1,4 glucosylated rebaudioside A, mono β-1,4 glucosylated rebaudioside B, mono β-1,4 glucosylated rebaudioside C, mono β-1,4 glucosylated rebaudioside D, mono β-1,4 glucosylated rebaudioside E, mono β-1,4 glucosylated rebaudioside F, mono β-1,4 glucosylated rebaudioside G, mono β-1,4 glucosylated rebaudioside M, mono β-1,4 glucosylated dulcoside A, mono β-1,4 glucosylated steviolbioside, and mono β-1,4 glucosylated rubusoside. In some further embodiments, the at one glucosylated terpene glycoside is selected from the group consisting of: mono β-1,4 cellobiosylated stevioside, mono β-1,4 cellobiosylated rebaudioside A, mono β-1,4 cellobiosylated rebaudioside B, mono β-1,4 cellobiosylated rebaudioside C, mono β-1,4 cellobiosylated rebaudioside D, mono β-1,4 cellobiosylated rebaudioside E, mono β-1,4 cellobiosylated rebaudioside F, mono β-1,4 cellobiosylated rebaudioside G, mono β-1,4 cellobiosylated rebaudioside M, mono β-1,4 cellobiosylated dulcoside A, mono β-1,4 cellobiosylated steviolbioside, and mono β-1,4 cellobiosylated rubusoside. In some embodiments thereof, the glucosylated terpene glycoside is a compound of the third aspect, or a compound of the fourth aspect, or a compound of the fifth aspect, or a compound of the sixth aspect. In some further embodiments of any of the foregoing embodiments, the glucosylated terpene glycosides in the composition confer, enhance, improve, or modify a sweet taste of a flavored article. In some such embodiments, the terpene glycosides are present in the composition in an amount effective to confer, enhance, improve, or modify the sweet taste of the composition. In some embodiments, the composition is a flavored article. In some embodiments, the composition is not a naturally occurring composition.

In an eighth aspect, the disclosure provides uses of any of the compounds of the third through the sixth aspects, or any compositions of the seventh aspect to modify the flavor of a composition, such as an ingestible composition. In some further embodiments, the use comprises enhancing the sweetness of an ingestible composition. In some other embodiments, the use comprises reducing the bitterness or reducing a lingering licorice taste of an ingestible composition. In some embodiments thereof, the composition comprises a sweetener, such as a non-caloric or caloric sweetener.

BRIEF DESCRIPTION OF DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
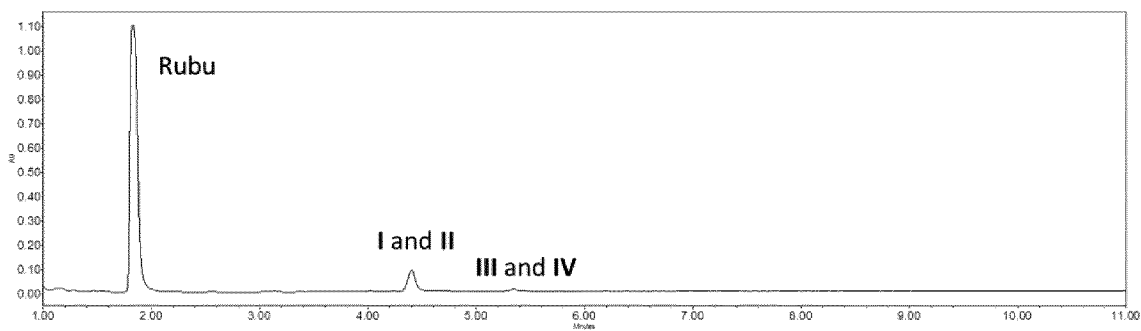
FIG. 1 shows an HPLC chromatogram of the product enzymatically generated by cellulase with Rubusoside (Rubu) and cellobiose as substrates.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

Methods

In certain aspects, the disclosure provides methods of making a glucosylated terpene glycoside, the method comprising: (a) providing an aqueous composition comprising a β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,4 glucosidic bond between the terpene glycoside moiety and one of the one or more β-glucosyl sugar moieties. In some embodiments, the reacting comprises incubating the aqueous composition.

In certain related aspects, the disclosure provides methods of reducing an unpleasant taste of a terpene glycoside, the method comprising: (a) providing an aqueous composition comprising an β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,4 glucosidic bond between the terpene glycoside moiety and one of the one or more β-glucosyl sugar moieties. In some embodiments, the reacting comprises incubating the aqueous composition.

In some embodiments of any of the foregoing aspects and embodiments, the terpene glycoside is stevioside, rebaudioside A, rebaudioside B, rebaudioside C, rebaudioside D, rebaudioside E, rebaudioside F, rebaudioside G, rebaudioside M, dulcoside A, steviolbioside, rubusoside, terpene glycosides found in *Stevia rebaudiana bertoni* plants, terpene glycosides found in *Rubus suavissimus* plants, terpene glycosides found in *Siraitis grosvenorii* plants, or mixtures thereof.

In some further embodiments, the starting material (e.g., the terpene glycoside) for the enzymatic process is an extract of a *Stevia rebaudiana bertoni* plant, an extract of a *Rubus suavissimus* plant, or an extract of a *Siraitis grosvenorii* plant. In some such embodiments, the plant extracts contain one or more than one terpene glycosides.

In one non-limiting example, *Stevia rebaudiana bertoni*, produces a number of diterpene glycosides, including stevioside, rebaudioside A, rebaudioside B, rebaudioside C, rebaudioside D, rebaudioside E, rebaudioside F, rebaudioside G, rebaudioside M, dulcoside A, and steviolbioside. In another non-limiting example, rubusoside is obtained from blackberry leaves (*Rubus suavissimus*) containing substantially a single terpene glycoside called rubusoside. In some other non-limiting examples, rubusoside is found in low amounts in stevia leaves. In some further such non-limiting examples, rubusoside is found in extracts of stevia leaves (*Stevia rebaudiana bertoni*).

In some embodiments, the starting material for the enzymatic process (e.g., the terpene glycoside) is a terpene glycoside purified from either an extract of a *Stevia rebau-*

*diana bertoni* plant, an extract of a *Rubus suavissimus* plant, or an extract of a *Siraitis grosvenorii* plant.

In some embodiments, the terpene glycoside starting material is selected from the group consisting of: stevioside, rebaudioside A, rebaudioside B, rebaudioside C, rebaudioside D, rebaudioside E, rebaudioside F, rebaudioside G, rebaudioside M, dulcoside A, steviolbioside, rubusoside, and mixtures thereof.

In some further embodiments, the terpene glycoside starting material is selected from the group consisting of: stevioside, rebaudioside A, rebaudioside B, rebaudioside C, and rubusoside.

In some embodiments, the terpene glycoside starting material is the starting material disclosed in U.S. Pat. No. 8,257,948.

In some embodiments, the terpene glycoside starting material is the starting material disclosed in PCT Publication No. WO 2017/089444.

In some embodiments, the terpene glycoside starting material is the starting material disclosed in PCT Publication No. WO 2013/019050.

In some embodiments, the terpene glycoside starting material is the starting material disclosed in European Patent Application Publication No. 3003058.

As used herein, the term "glycoside" refers to an organic compound to which one or more sugar units are covalently bound at one or more sites of the chemical structure.

In some embodiments, the aqueous composition comprises deionized water. Alternatively, in some embodiments, the aqueous composition comprises sodium acetate. In some embodiments of any of the foregoing embodiments, the aqueous composition is a solution.

The aqueous composition can have any suitable pH. In some embodiments, the pH of the aqueous composition ranges from pH 4.0 to pH 7.0. In some embodiments, the pH of the aqueous composition ranges from pH 4.0 to pH 6.0. In some embodiments, the pH of the aqueous composition ranges from pH 4.0 to pH 5.0. In some embodiments, the pH of the aqueous composition ranges from pH 5.0 to pH 7.0. In some embodiments, the pH of the aqueous composition ranges from pH 6.0 to pH 7.0. In some embodiments, the pH of the aqueous composition is pH 4.0, or 4.1, or 4.2, or 4.3, or 4.4, or 4.5, or 4.6, or 4.7, or 4.8, or 4.9, or 5.0, or 5.1, or 5.2, or 5.3, or 5.4, or 5.5, or 5.6, or 5.7, or 5.8, or 5.9, or 6.0, or 6.1, or 6.2, or 6.3, or 6.4, or 6.5, or 6.6, or 6.7, or 6.8, or 6.9, or 7.0. In some such embodiments, the pH of the aqueous composition is pH of about 5.0.

In the methods disclosed herein, the terpene glycoside can be added to the aqueous composition in any suitable concentration. In some embodiments, the terpene glucoside is added to the aqueous composition at a concentration of from 0.005 g/mL to 0.5 g/mL. In some embodiments, the terpene glucoside is added to the aqueous composition at a concentration of from 0.05 mL to 0.25 g/mL. In some embodiments, the terpene glucoside is added to the aqueous composition at a concentration of from 0.1 g/mL to 0.2 g/mL.

In the methods disclosed herein, any suitable beta-glucosyl sugar compound can be used. In some embodiments, the beta-glucosyl sugar compound is a reducing sugar comprising two β-glucose molecules linked by a β-1,4 bond. In some embodiments, the beta-glucosyl sugar compound is selected from the group consisting of: cellobiose, cellotriose, cellotetraose, cellopentaose, and cellohexaose. In some embodiments, the beta-glucosyl sugar compound is selected from the group consisting of: cellotriose, cellotetraose, cellopentaose, and cellohexaose. In some embodiments, the beta-glucosyl sugar compound is cellobiose. In some embodiments, the beta-glucosyl sugar compound is a cellodextrin. In some embodiments, the beta-glucosyl sugar compound is a cellulose, or a derivative thereof. In some embodiments, the beta-glucosyl sugar compound is cellobiose.

In the methods disclosed herein, the beta-glucosyl sugar compound can be added to the aqueous composition in any suitable concentration. In some embodiments, the concentration of the beta-glucosyl sugar compound in the aqueous composition ranges from 10% to 40% (wt/wt), or from 20% to 30% (wt/wt). In some embodiments, the concentration of the beta-glucosyl sugar compound in the aqueous composition ranges from 0.005 g/mL to 0.5 g/mL. In some embodiments, the concentration of the beta-glucosyl sugar compound in the aqueous composition is about 0.2 g/mL.

In the methods disclosed herein, the terpene glycoside can be present in the aqueous composition at any suitable ratio relative to the beta-glucosyl sugar compound. In some embodiments, the ratio (wt/wt) of the terpene glycoside to the beta-glucosyl sugar compound in the aqueous composition ranges from 100:1 to 1:100. In some embodiments, the ratio (wt/wt) of the terpene glycoside to the beta-glucosyl sugar compound in the aqueous composition ranges from 10:1 to 1:10. In some embodiments, the ratio (wt/wt) of the terpene glycoside to the beta-glucosyl sugar compound in the aqueous composition is about 1:1.

In some embodiments, cellulase is present in the aqueous composition and performs a transglucosylation reaction, thereby generating glucosylated terpene glycoside having a single glucosyl residue linked to the terpene glycoside via a β-1,4 glucosidic bond. In some embodiments, the transglucosidase performs a transglucosylation reaction, thereby generating a glucosylated terpene glycoside having one or more glucose residues covalently attached to the terpene glycoside via a β-1,4 glucosidic bond. In some embodiments, the number of glucose residues that are added to the terpene glycoside is controlled by parameters such as, for example, the time of the reaction, the temperature of the reaction, the concentration of the terpene glycoside, the concentration of the beta-glucosyl sugar compound, and the like.

In some embodiments, the cellulase performs the transglucosylation reaction, using cellobiose as a substrate, thereby generating a glucosylated terpene glycoside wherein two glucose units are added to the terpene glycoside via a β-1,4 glucosidic bond. In some embodiments, the cellulase performs a transglucosylation reaction, thereby generating glucosylated terpene glycoside having a single cellobiosyl residue linked to the terpene glycoside via a β-1,4 glucosidic bond. In some embodiments, the transglucosidase performs a transglucosylation reaction, thereby generating a glucosylated terpene glycoside having one or more cellobiosyl residues covalently attached to the terpene glycoside via a β-1,4 glucosidic bond. In some embodiments, the number of cellobiosyl residues that are added to the terpene glycoside is controlled by parameters such as, for example, the time of the reaction, the temperature of the reaction, the concentration of the terpene glycoside, the concentration of the beta-glucosyl sugar compound, and the like.

In some embodiments, the cellulase is in a form of cell-free culture broth, concentrated liquid cell-free culture broth, spray dried or freeze dried cell-free culture broth, or high purity protein. Free and immobilized enzyme preparations may also be used.

Any suitable cellulase can be used. As used herein, the term "cellulase" include endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulose (CMCase), avicelase, celludextrinase, cellulase A, cellulosin AP, alkali cellulase, cellulase A 3, 9.5 cellulase, beta-glucosidase, cellulose 1,4-beta-cellobiosidase, and pancellase SS.

The cellulase can be added at any suitable concentration. In some embodiments, the cellulase is added to the aqueous composition at an concentration ranging from 0.2 to 0.4 units per gram of beta-glucosyl sugar compound. In some embodiments, the cellulase is added to the aqueous composition at a concentration ranging from 2 mg/mL to 200 mg/mL. In some embodiments, the cellulase is added to the aqueous composition at c concentration of about 40 mg/mL.

In the methods disclosed herein, the terpene glycoside can be used at any suitable concentration relative to the cellulase enzyme. In some embodiments, the ratio (w/w) of the terpene glycoside to the cellulase enzyme in the aqueous composition ranges from 100:1 to 1:100, or from 10:1 to 1:10. In some embodiments, the ratio (w/w) of the terpene glycoside to the cellulase enzyme in the aqueous composition is about 1:1.

In some embodiments, the ratio of the amount of cellulase enzyme in wt % relative to the amount of terpene glycoside ranges from 0.1% to 100%, or from 1% to 50%, or from 10% to 20%.

In some embodiments, the mixture containing the cellulase is incubated, e.g., for a time and temperature sufficient to generate the glucosylated terpene glycoside. In some embodiments, the glucosylated terpene glycoside is a glucosylated terpene glycoside having a single glucosyl residue linked to the terpene glycoside via a β-1,4 glucosidic bond. Alternatively, in some embodiments, the glucosylated terpene glycoside is a glucosylated terpene glycoside having a single cellobiosyl residue linked to the terpene glycoside via a β-1,4 glucosidic bond. In some embodiments, the mixture containing the cellulase is incubated for a time and temperature sufficient to generate the glucosylated terpene glycoside having a single cellobiosyl residue linked to the terpene glycoside via a β-1,4 glucosidic bond.

Any suitable temperature can be used for the incubation. In some embodiments, the temperature ranges from 30 to 90° C., or from 70 to 90° C. In some embodiments, the temperature is about 60° C. In some embodiments, the temperature is about 37° C.

The incubation can be carried out for any suitable length of time. In some embodiments, the time sufficient is 24 hours or greater. In some embodiments, the time sufficient is 24 hours, or less. In some embodiments, the time sufficient is 24 hours, or 23 hours, or 22 hours, or 21 hours, or 20 hours, or 19 hours, or 18 hours, or 17 hours, or 16 hours, or 15 hours, or 14 hours, or 13 hours, or 12 hours, or 11 hours, or 10 hours, or 9 hours, or 8 hours, or 7 hours, or 6 hours, or 5 hours, or 4 hours, or 3 hours, or 2 hours, or 1 hour. In some embodiments, the time sufficient is about 24 hours.

In some embodiments, after the incubation step, the mixture containing the glucosylated terpene glycoside may treated further. Such further treatment may include, for example, an inactivation step or a purification step, wherein the glucosylated terpene glycoside is isolated or purified. In some aspects, the glucosylated terpene glycoside is a glucosylated terpene glycoside having a single glucosyl residue linked to the terpene glycoside via a β-1,4 glucosidic bond. Alternatively, in some aspects, the glucosylated terpene glycoside is a glucosylated terpene glycoside having a single cellobiosyl residue linked to the terpene glycoside via a β-1,4 glucosidic bond.

Non-limiting examples of the purification step include enrichment, isolation, or purification of the glucosylated terpene glycoside, or the removal of solids from the reaction mixture. In some embodiments, the glucosylated terpene glycoside is a glucosylated terpene glycoside having a single glucosyl residue linked to the terpene glycoside via a β-1,4 glucosidic bond. Alternatively, in some embodiments, the glucosylated terpene glycoside is a glucosylated terpene glycoside having a single cellobiosyl residue linked to the terpene glycoside via a β-1,4 glucosidic bond.

In some embodiments, solids are removed from the reaction mixture by means such as filtration, centrifugation, or other techniques known to those skilled in the art. In some embodiments, carbohydrates are removed from the mixture using adsorption resins, precipitation, or other techniques known to those skilled in the art. In some embodiments, the further treatment includes inactivating the cellulase. In one such example, the cellulase is inactivated by the application of heat. In some embodiments, the cellulase is inactivated by heating the reaction mixture to a temperature sufficient to inactivate the cellulase. In some such embodiments, the temperature sufficient is 100° C.

U.S. Pat. No. 8,257,948 discloses some examples of purification steps that may be utilized in some aspects of the present disclosure to isolate or purify the glucosylated terpene glycoside.

PCT Publication No. WO 2017/089444 discloses other examples of purification steps that may be utilized in some aspects of the present disclosure to isolate or purify the glucosylated terpene glucoside.

PCT Publication No. WO 2013/019050 discloses other examples of purification steps that may be utilized in some aspects of the present disclosure to isolate or the glucosylated terpene glycoside.

European Patent Application Publication No. 3003058 discloses other examples of purification steps that may be utilized in some aspects of the present disclosure to isolate or purify the glucosylated terpene glycoside.

U.S. Pat. No. 8,257,948 discloses some examples of inactivation steps that may be utilized in some aspects of the present disclosure.

PCT Publication No. WO 2017/089444 discloses other examples of inactivation steps that may be utilized in some aspects of the present disclosure.

Glucosylated Terpene Glycosides

In some embodiments, the glucosylated terpene glycoside is selected from the group consisting of: mono β-1,4 glucosylated stevioside, mono β-1,4 glucosylated rebaudioside A, mono β-1,4 glucosylated rebaudioside B, mono β-1,4 glucosylated rebaudioside C, mono β-1,4 glucosylated rebaudioside D, mono β-1,4 glucosylated rebaudioside E, mono β-1,4 glucosylated rebaudioside F, mono β-1,4 glucosylated rebaudioside G, mono β-1,4 glucosylated rebaudioside M, mono β-1,4 glucosylated dulcoside A, mono β-1,4 glucosylated steviolbioside, mono β-1,4 glucosylated rubusoside, and mixtures thereof.

In some embodiments, the glucosylated terpene glycoside is selected from the group consisting of: di β-1,4 glucosylated stevioside, di β-1,4 glucosylated rebaudioside A, di β-1,4 glucosylated rebaudioside B, di β-1,4 glucosylated rebaudioside C, di β-1,4 glucosylated rebaudioside D, di β-1,4 glucosylated rebaudioside E, di β-1,4 glucosylated rebaudioside F, di β-1,4 glucosylated rebaudioside G, di β-1,4 glucosylated rebaudioside M, di β-1,4 glucosylated dulcoside A, di β-1,4 glucosylated steviolbioside, di β-1,4 glucosylated rubusoside, and mixtures thereof.

In some embodiments, the glucosylated terpene glycoside is selected from the group consisting of: mono β-1,4 cellobiosylated stevioside, mono β-1,4 cellobiosylated rebaudioside A, mono β-1,4 cellobiosylated rebaudioside B, mono β-1,4 cellobiosylated rebaudioside C, mono β-1,4 cellobiosylated rebaudioside D, mono β-1,4 cellobiosylated rebaudioside E, mono β-1,4 cellobiosylated rebaudioside F, mono β-1,4 cellobiosylated rebaudioside G, mono β-1,4 cellobiosylated rebaudioside M, mono β-1,4 cellobiosylated dulcoside A, mono β-1,4 cellobiosylated steviolbioside, and mono β-1,4 cellobiosylated rubusoside.

In certain aspects, the disclosure provides a compound of formula I:

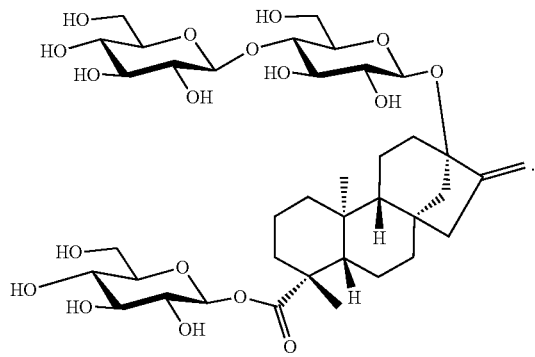

I

In certain aspects, the disclosure provides a compound of formula II:

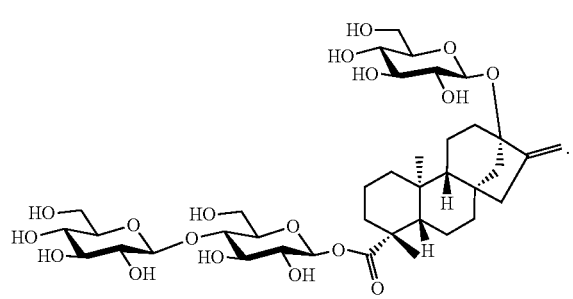

II

In certain aspects, the disclosure provides a compound of formula III:

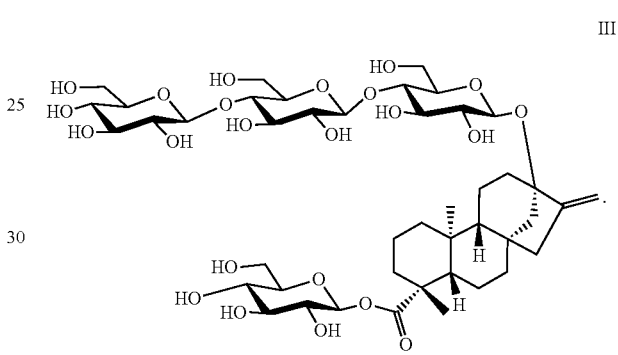

III

In certain aspects, the disclosure provides a compound of formula IV:

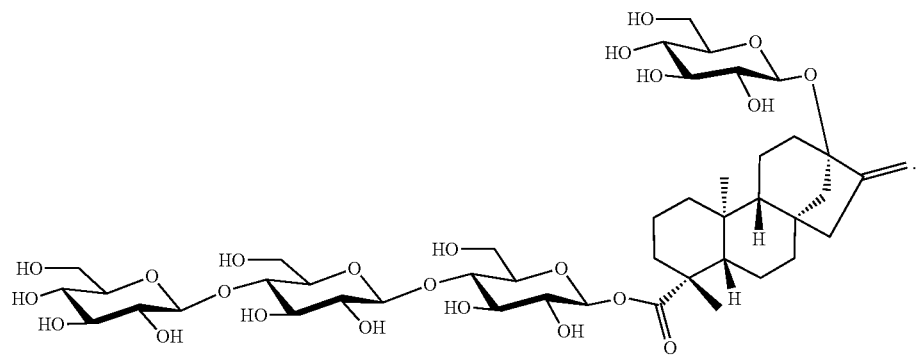

IV

As used herein, the foregoing compounds of formulas I to IV can also be referred to as "Compound I," "Compound II," "Compound III," and "Compound IV," respectively.

In certain aspects, the disclosure provides compositions comprising at least one glucosylated terpene glycoside selected from the group consisting of: mono β-1,4 glucosylated stevioside, mono β-1,4 glucosylated rebaudioside A, mono β-1,4 glucosylated rebaudioside B, mono β-1,4 glucosylated rebaudioside C, mono β-1,4 glucosylated rebaudioside D, mono β-1,4 glucosylated rebaudioside E, mono β-1,4 glucosylated rebaudioside F, mono β-1,4 glucosylated rebaudioside M, mono β-1,4 glucosylated dulcoside A, mono β-1,4 glucosylated steviolbioside, mono β-1,4 glucosylated rubusoside, di β-1,4 glucosylated stevioside, di β-1,4 glucosylated rebaudioside A, di β-1,4 glucosylated rebaudioside B, di β-1,4 glucosylated rebaudioside C, di β-1,4 glucosylated rebaudioside D, di β-1,4 glucosylated rebaudioside E, di β-1,4 glucosylated rebaudioside F, di β-1,4 glucosylated rebaudioside M, di β-1,4 glucosylated dulcoside A, di β-1,4 glucosylated steviolbioside, di β-1,4 glucosylated rubusoside, mono β-1,4 cellobiosylated stevioside, mono β-1,4 cellobiosylated rebaudioside A, mono β-1,4 cellobiosylated rebaudioside B, mono β-1,4 cellobiosylated rebaudioside C, mono β-1,4 cellobiosylated rebaudioside D, mono β-1,4 cellobiosylated rebaudioside E, mono β-1,4 cellobiosylated rebaudioside F, mono β-1,4 cellobiosylated rebaudioside M, mono β-1,4 cellobiosylated dulcoside A, mono β-1,4 cellobiosylated steviolbioside, and mono β-1,4 cellobiosylated rubusoside.

In some embodiments, the composition comprises at least one glucosylated terpene glycoside selected from the group consisting of: the compound of formula I, the compound of formula II, the compound of formula III, and the compound of formula IV.

In some embodiments, the composition comprises at least one glucosylated terpene glycoside having a single glucosyl residue linked to the terpene glycoside via a β-1,4 glucosidic bond selected from the group consisting of: the compound of formula I and the compound of formula II.

In some embodiments, the composition comprises at least one glucosylated terpene glycoside having a single cellobiosylated residue linked to the terpene glycoside via a β-1,4 glucosidic bond selected from the group consisting of: the compound of formula III and the compound of formula IV.

Sweeteners or Sweetness Enhancers

The one glucosylated terpene glycoside described herein may be used as sweetness enhancers, flavor enhancers, taste maskers, or sweeteners in various flavored articles. In some embodiments, the glucosylated terpene glycoside is a glucosylated terpene glycoside having a single glucosyl residue linked to the terpene glycoside via a β-1,4 glucosidic bond. Alternatively, in some embodiments, the glucosylated terpene glycoside is a glucosylated terpene glycoside having a single cellobiosyl residue linked to the terpene glycoside via a β-1,4 glucosidic bond.

In certain aspects, the disclosure provides the use of at least one glucosylated terpene glycoside of the foregoing aspects and embodiments to confer, enhance, improve, or modify a sweet taste of a flavored article. In some embodiments, the glucosylated terpene glycoside is a glucosylated terpene glycoside having a single glucosyl residue linked to the terpene glycoside via a β-1,4 glucosidic bond. Alternatively, in some embodiments, the glucosylated terpene glycoside is a glucosylated terpene glycoside having a single cellobiosyl residue linked to the terpene glycoside via a β-1,4 glucosidic bond.

In certain aspects, the disclosure provides the use of at least one glucosylated terpene glycoside according to some aspects presented herein to mask a lingering taste of a flavored article. In some embodiments, the glucosylated terpene glycoside is a glucosylated terpene glycoside having a single glucosyl residue linked to the terpene glycoside via a β-1,4 glucosidic bond. Alternatively, in some embodiments, the glucosylated terpene glycoside is a glucosylated terpene glycoside having a single cellobiosyl residue linked to the terpene glycoside via a β-1,4 glucosidic bond.

In certain aspects, the disclosure provides a method, wherein the method confers, enhances, improves, or modifies a sweet taste of a flavored article, wherein the method comprises adding at least one glucosylated terpene glycoside having a single glucosyl residue linked to the terpene glycoside via a β-1,4 glucosidic bond according to some aspects presented herein to the flavored article, in an amount effective to confer, enhance, improve, or modify the sweet taste of the flavored article.

In certain aspects, the disclosure provides a method, wherein the method masks a lingering taste of a flavored article, wherein the method comprises adding the glucosylated terpene glycoside having a single glucosyl residue linked to the terpene glycoside via a β-1,4 glucosidic bond according to some aspects presented herein to the flavored article, in an amount effective to mask the lingering taste of a flavored article.

In certain aspects, the disclosure provides a method, wherein the method confers, enhances, improves, or modifies a sweet taste of a flavored article, wherein the method comprises adding at least one glucosylated terpene glycoside having a single cellobiosyl residue linked to the terpene glycoside via a β-1,4 glucosidic bond according to some aspects presented herein to the flavored article, in an amount effective to confer, enhance, improve, or modify the sweet taste of the flavored article.

In certain aspects, the disclosure provides a method, wherein the method masks a lingering taste of a flavored article, wherein the method comprises adding the glucosylated terpene glycoside having a single cellobiosyl residue linked to the terpene glycoside via a β-1,4 glucosidic bond according to some aspects presented herein to the flavored article, in an amount effective to mask the lingering taste of a flavored article.

In some embodiments, the amount effective to confer, enhance, improve, or modify the sweet taste of the flavored article is about 40 ppm, such as from 30 ppm to 50 ppm, or from 20 ppm to 60 ppm, or from 10 ppm to 70 ppm. In some embodiments, the amount effective to confer, enhance, improve, or modify the sweet taste of the flavored article is less than 40 ppm. In some aspects, the amount effective to confer, enhance, improve, or modify the sweet taste of the flavored article is greater than 40 ppm. In some embodiments, the amount effective to confer, enhance, improve, or modify the sweet taste of the flavored article is from 0 and 1000 ppm.

In some aspects, the disclosure provides flavored articles that comprise: the least one glucosylated terpene glycoside (of the foregoing aspects and embodiments); and a foodstuff base, wherein the glucosylated terpene glycoside is selected from the group consisting of: a glucosylated terpene glycoside having a single glucosyl residue linked to the terpene glycoside via a β-1,4 glucosidic bond, and a glucosylated terpene glycoside having a single cellobiosyl residue linked to the terpene glycoside via a β-1,4 glucosidic bond.

Suitable foodstuffs, e.g. foods or beverages are also provided herein. For the purpose of the present disclosure, "foodstuff base" means an edible product, e.g. a food or a beverage. Therefore, a flavored article provided herein comprises the functional formulation, as well as optionally additional benefit agents, corresponding to a desired edible product, e.g., a savory cube, and a flavor effective amount of the least one glucosylated terpene glycoside described herein. In some aspects, the glucosylated terpene glycoside is a glucosylated terpene glycoside having a single glucosyl residue linked to the terpene glycoside via a β-1,4 glucosidic bond. Alternatively, in some aspects, the glucosylated terpene glycoside is a glucosylated terpene glycoside having a single cellobiosyl residue linked to the terpene glycoside via a β-1,4 glucosidic bond.

The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

The food product may be selected from the group consisting of condiments, baked goods, powdery food, bakery filings and fluid dairy products.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

Fluid dairy products include, without limitation, non-frozen, partially frozen and frozen fluid dairy products such as, for example, milks, ice creams, sorbets and yogurts. Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra-high temperature, ohmic heating or commercial aseptic sterilization) and hot-filled packaging; and cold-filled products made through filtration or other preservation techniques.

The nature and type of the constituents of the foodstuffs or beverages do not warrant a more detailed description here, which in any case would not be exhaustive, the skilled person being able to select them on the basis of his general knowledge and according to the nature of the product.

The proportions in which the least one glucosylated terpene glycoside described herein can be incorporated into the various aforementioned articles or compositions vary within a wide range of values. These values are dependent on the nature of the article to be flavored and on the desired organoleptic effect as well as the nature of the co-ingredients in a given base when the compounds according to the invention are mixed with flavoring co-ingredients, solvents or additives commonly used in the art.

In the case of flavoring compositions, typical concentrations are in the order of about 0.0001 wt % to 1 wt %, or even more, of the least one glucosylated terpene glycoside described herein based on the weight of the consumer product into which they are incorporated. Concentrations lower than these, such as in the order of 0.001 wt % to 0.5 wt % by weight, can be used when the least one glucosylated terpene glycoside described herein are incorporated into flavored articles, percentage being relative to the weight of the article.

EXAMPLES

Example 1: Generation of Mono β-1,4-Glucosylated Terpene Glycoside Compounds (Compounds I and II) Using Rubusoside as a Starting Material by a Method According to Some Aspects Presented Herein Rubusoside (1 g) and cellobiose (1 g) were dissolved in 10 ml NaOAc—HOAc (pH=5.0, 0.2 M, 5 mL) buffer at room temperature. Subsequently, 200 mg cellulase (Aladdin) was added to the mixture. The mixture containing the enzyme was then heated to 37° C., and the mixture containing the enzyme was incubated at 37° C. for 24 hours to allow the transglucosidation reaction to proceed, thereby generating the at least one glucosylated terpene glycoside having a single glucosyl residue linked to the terpene glycoside via a β-1,4 glucosidic bond. The reaction was terminated by inactivating the cellulase by incubating the reaction mixture at 100° C. for 30 minutes.

The resulting reaction mixture was analyzed by UPLC-UV, and a mixture containing glucosylated terpene glycosides having a single glucosyl residue linked to the terpene glycoside via a β-1,4 glucosidic bond was identified (See FIG. 1). The identified mixture was purified via a prep-LC. The compounds within the mixture were identified as compounds I and II, at a ratio of 2:1.

The resulting reaction mixture was analyzed by UPLC-UV, and a mixture containing glucosylated terpene glycosides having a single cellobiosyl residue linked to the terpene glycoside via a β-1,4 glucosidic bond was identified (See FIG. 1). The identified mixture was purified via a prep-LC. The compounds within the mixture were identified as the compound of formula III and the compound of formula IV, at a ratio of 4:1.

Figure 2:
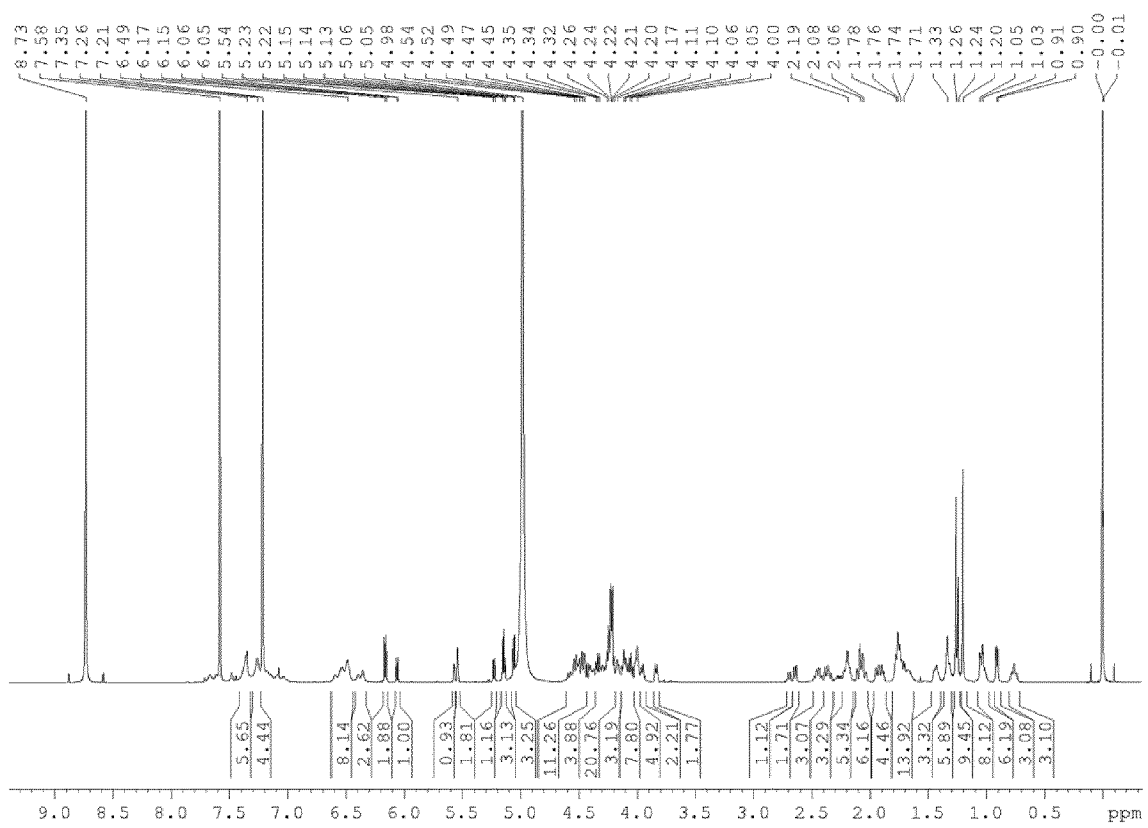
FIG. 2 shows A $^1$H NMR spectrum for a composition comprising a mixture of the compound of formula I and the compound of formula II.
Figure 3:
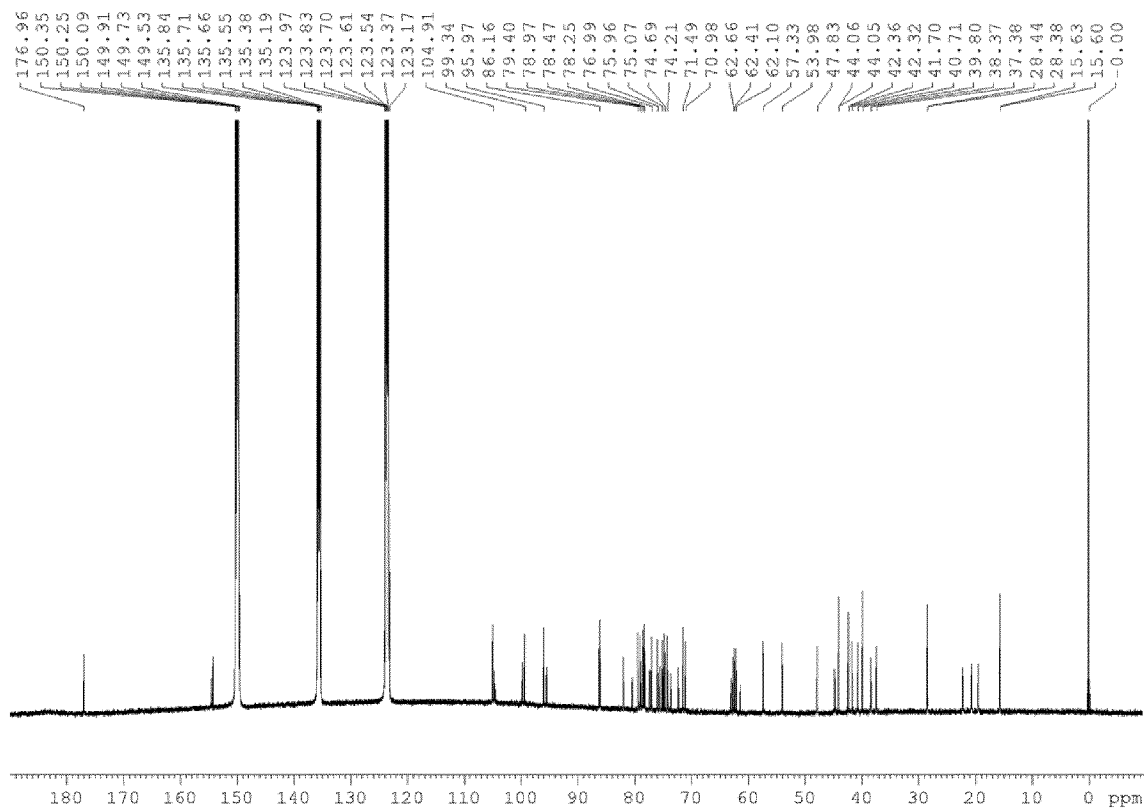
FIG. 3 shows A $^{13}$C NMR spectrum for a composition comprising a mixture of the compound of formula I and the compound of formula II.

FIG. 2 shows A $^1$H NMR spectrum for a composition comprising a mixture of the compound of formula I and the compound of formula II. FIG. 3 shows A $^{13}$C NMR spectrum for a composition comprising a mixture of the compound of formula I and the compound of formula II.

Example 2: Sensory Properties of a Composition Comprising Compounds I and II

A composition comprising a mixture of the compound of formula I and the compound of formula II at a ratio (w/w) of 2:1 was generated according to the methods described in Example 1. The composition was dissolved in either a (i) 4% w/w sucrose solution, or (ii) a 0.02% w/w 95% steviol glycoside solution. A panel of 25 trained people evaluated the test solutions for taste properties (sweet, licorice and sweet lingering) on a scale of −5 to 5 (−5 denoted no effect and 5 denoted extremely strong effect, 0 being the intensity of a reference water solution containing either (i) 4% w/w sucrose solution, or (ii) a 0.02% w/w 95% steviol glycoside solution.) The results are shown in the table below.

| Matrix | Taste | With nose-clip (NC) | Without nose-clip (WNC) | Significant level Student test NC | Significant level Student test WNC |
|---|---|---|---|---|---|
| Sucrose 4% | sweetness | 0.73 | 0.78 | *** | *** |
| SG95 0.02% | sweetness | 0.25 | 0.16 | | |
| SG95 0.02% | licorice | 0.22 | 0.22 | | |
| SG95 0.02% | lingering | −0.33 | −0.03 | * | |

These data suggest that the composition comprising Compounds I and II at a ratio of 2:1 significantly enhanced the sweet intensity of the 4% w/w sucrose solution (at 99.9% of confidence level), with and without a nose-clip. The composition comprising the compound of formula I and the compound of formula II at a ratio of 2:1 significantly decreases the lingering intensity (at 95% confidence level) with nose-clip, and slightly affected the sweet, licorice intensities in the 0.02% SG95 base.

Example 3: Sensory Properties of a Composition Comprising the at Least One Mono β-1,4-glucosylated Terpene Glycosides Presented Herein A composition comprising the at least one glucosylated terpene glucosides may be generated according to the methods described in Example 1. The composition may be dissolved in either (i) water, or (ii) a 4% w/w sucrose solution, or (iii) 7% (w/w) inverted sugar plus 0.15% citric acid (w/w) solution wherein the final concentration of the composition in solution may range from 0 to 1000 ppm. Corresponding control solutions of either (i) 1.5%, or (ii) 4% w/w sucrose, or (iii) 7% (w/w) inverted sugar plus 0.15% citric acid (w/w) solution will also be generated. A panel of 10 experts will evaluate the difference between solution of the test composition and the sucrose solutions, using the 3-Alternative Forced Choice (3-AFC) or sweetness intensity scale method. All samples will be tested in blind in a random order.

The invention claimed is:

1. A compound, which is a compound of formula I, a compound of formula III, or a compound of formula IV:

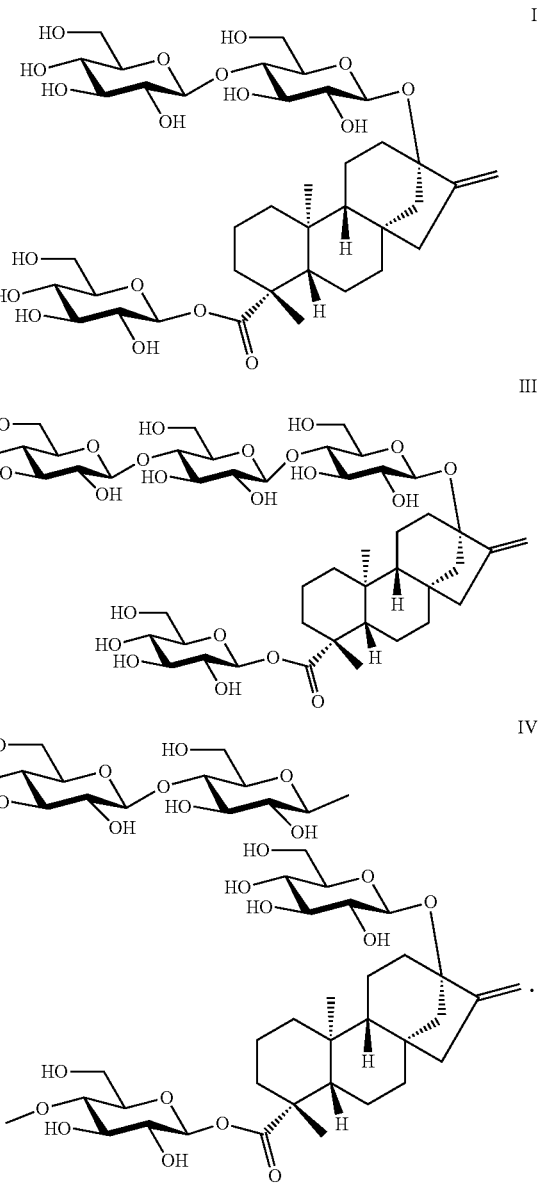

2. A method of modifying the flavor of a flavored article, the method comprising introducing the glucosylated terpene glycoside of claim 1 to a flavored composition.

3. The method of claim 2, wherein the method is a method of enhancing a sweet taste of the flavored article.

4. A flavored article, which comprises a carrier and the glucosylated terpene glycoside of claim 1.

* * * * *